US010436763B2

(12) United States Patent
Behle et al.

(10) Patent No.: US 10,436,763 B2
(45) Date of Patent: *Oct. 8, 2019

(54) OIL QUALITY SENSOR AND ADAPTER FOR DEEP FRYERS

(71) Applicant: FRYMASTER L.L.C., Shreveport, LA (US)

(72) Inventors: Martin Behle, Remscheid (DE); Jan Claesson, Land O'Lakes, FL (US); Janice M. K. Jaferian, Palm Harbor, FL (US)

(73) Assignee: Frymaster L.L.C., Shreveport, LA (US)

( * ) Notice: Subject to any disclaimer, the term of this patent is extended or adjusted under 35 U.S.C. 154(b) by 192 days.

This patent is subject to a terminal disclaimer.

(21) Appl. No.: 15/291,140

(22) Filed: Oct. 12, 2016

(65) Prior Publication Data

US 2017/0030880 A1 Feb. 2, 2017

Related U.S. Application Data

(63) Continuation of application No. 13/923,418, filed on Jun. 21, 2013, now Pat. No. 9,510,708, which is a
(Continued)

(51) Int. Cl.
*G01R 27/26* (2006.01)
*G01R 27/08* (2006.01)
(Continued)

(52) U.S. Cl.
CPC .......... *G01N 33/03* (2013.01); *A47J 37/1223* (2013.01); *A47J 37/1266* (2013.01);
(Continued)

(58) Field of Classification Search
CPC .... G01N 33/03; G01N 33/2888; G01N 27/02; G01N 27/06; G01N 27/22; G01N 27/221;
(Continued)

(56) References Cited

U.S. PATENT DOCUMENTS

| 4,148,729 A | 4/1979 | Howard |
| 4,282,423 A * | 8/1981 | Volz ........................ G05D 23/24 219/442 |

(Continued)

FOREIGN PATENT DOCUMENTS

| DE | 19649510 A1 | 6/1998 |
| EP | 1 324 036 A2 | 7/2003 |

(Continued)

OTHER PUBLICATIONS

Written Opinion of the International Preliminary Examining Authority dated Dec. 26, 2012 for International Patent Application No. PCT/US201 0/038685 consisting of 7 pages.
(Continued)

*Primary Examiner* — Hoai-An D. Nguyen
(74) *Attorney, Agent, or Firm* — Ohlandt, Greeley, Ruggiero & Perle, L.L.P.

(57) ABSTRACT

A system for measuring the state of degradation of cooking oil or fat includes at least one fryer pot. A conduit is fluidly connected to the fryer pot for transporting cooking oil from the fryer pot and returning the cooking oil back to the fryer pot. A pump is provided for re-circulating cooking oil to and from the fryer pot. A sensor is disposed in fluid communication with the conduit and measures an electrical property of the cooking oil as the cooking oil flows past the sensor and is returned to the at least one fryer pot.

18 Claims, 7 Drawing Sheets

Related U.S. Application Data continuation of application No. 12/456,389, filed on Jun. 16, 2009, now Pat. No. 8,497,691, which is a continuation-in-part of application No. 12/215,307, filed on Jun. 26, 2008, now abandoned.

(60) Provisional application No. 60/995,527, filed on Sep. 27, 2007, provisional application No. 60/937,513, filed on Jun. 28, 2007.

(51) Int. Cl.
| | | |
|---|---|---|
| *G01N 33/03* | (2006.01) | |
| *A47J 37/12* | (2006.01) | |
| *G01N 21/53* | (2006.01) | |
| *G01N 27/22* | (2006.01) | |
| G01R 27/22 | (2006.01) | |
| G01R 27/02 | (2006.01) | |

(52) U.S. Cl.
CPC ........ *A47J 37/1271* (2013.01); *G01N 21/534* (2013.01); *G01N 27/22* (2013.01); *G01R 27/26* (2013.01); *G01R 27/02* (2013.01); *G01R 27/22* (2013.01)

(58) Field of Classification Search
CPC ...... G01N 27/26; G01N 21/534; G01R 27/02; G01R 27/22; G01R 27/26; G01R 27/2605; G01D 5/24; G01D 5/241; G01D 5/2412; G01D 5/2417; A61B 5/0537; A47J 37/1223; A47J 37/1266; A47J 37/1271
USPC ...... 324/71.1, 444, 600, 649, 658, 663, 691, 324/692, 693, 698
See application file for complete search history.

(56) References Cited

U.S. PATENT DOCUMENTS

| | | | |
|---|---|---|---|
| 4,974,501 A | 12/1990 | Grob et al. | |
| 5,071,527 A | 12/1991 | Kauffman | |
| 5,194,910 A | 3/1993 | Kirkpatrick, Jr. et al. | |
| 5,589,935 A | 12/1996 | Biard | |
| 5,680,811 A | 10/1997 | Highnote et al. | |
| 5,776,530 A | 7/1998 | Davis et al. | |
| 5,787,372 A | 7/1998 | Edwards et al. | |
| 5,818,731 A | 10/1998 | Mittal et al. | |
| 5,942,269 A | 8/1999 | Casey et al. | |
| 6,091,484 A | 7/2000 | Venica et al. | |
| 6,127,185 A * | 10/2000 | Melton ................ | G01N 27/06 324/71.1 |
| 6,254,790 B1 | 7/2001 | King et al. | |
| 6,717,667 B2 | 4/2004 | Varghese et al. | |
| 6,777,009 B1 * | 8/2004 | Shealy ............... | A47J 37/1266 426/231 |
| 6,822,461 B2 | 11/2004 | Kluen | |
| 7,030,629 B1 | 4/2006 | Stahlmann et al. | |
| 7,262,844 B2 | 8/2007 | Larsen et al. | |
| 7,309,422 B2 | 12/2007 | Mullaney, Jr. | |
| 7,504,836 B2 | 3/2009 | Chambon et al. | |
| 7,523,646 B2 | 4/2009 | Klun | |
| 7,612,874 B2 | 11/2009 | Kong et al. | |
| 7,659,731 B2 * | 2/2010 | Lin .................... | G01N 33/2852 324/439 |
| 7,834,646 B2 | 11/2010 | Chambon et al. | |
| 8,497,691 B2 | 6/2013 | Behle et al. | |
| 2002/0035931 A1 | 3/2002 | Tschopp et al. | |
| 2004/0007137 A1 | 1/2004 | Hwang | |
| 2005/0066711 A1 | 3/2005 | Discenzo | |
| 2006/0091050 A1 | 5/2006 | Hwang | |
| 2006/0272415 A1 | 12/2006 | Liu et al. | |
| 2015/0374173 A1 | 12/2015 | McGhee et al. | |

FOREIGN PATENT DOCUMENTS

| | | |
|---|---|---|
| EP | 1 439 388 A1 | 7/2004 |
| JP | 2005055198 A | 3/2005 |
| WO | 2000020034 A1 | 1/2000 |
| WO | 2008/135368 A1 | 11/2008 |
| WO | 2009/005691 A1 | 1/2009 |

OTHER PUBLICATIONS

Writien Opinion of the IPEA Per Form 408ISSUED dated Aug. 10, 2012 in the PCT/ US201 0/038885.
First Office Action dated Dec. 7, 2010 in Chinese Application 200880021791.9.
Second Office Action dated Aug. 25, 2011 in Chinese Application 200880021791.9.
Extended European Search Report dated Sep. 2, 2011 in EP 08768792.7.
Jayadeep Vijayan et al.; "Optical Properties of Corn Oild During Frying" International Journal of Food Science and Technology vol. 31 Jan. 1, 1996 pp. 353-358 XP55005538.(Abstract).
Xin-Qing Xu; "A New Spectrophotometric Method for the Rapid Assessment of Deep Frying Oil Quaolity"; Journal of the American Oil Chemists' Society vol. 77 No. 10 Jan. 1, 2006 pp. 1083-1086 XPXP55005591.
Written Opinion Form IPEA 408 dated Dec. 5, 2011 With New Art in PCT/ D US201 0/038885.
Extended European Search Report and European Search Opinion dated Feb. 28, 2014 from EP Application No. 13188273.0, 6 pages.
Extended European Search Report and European Search Opinion dated Dec. 15, 2015 from EP Application No. 15178685.2, 8 pages.
C.W. Fritsch et al., "Changes in Dielectric Constant as a Measure of Frying Oil Deterioration", J. of the Am. Oil Chemists' Soc'y, vol. 56, Issue 8, 746-50 (1979), 5 Page(s).
European Office Action dated Jul. 25, 2018 for European application No. 15 178 685.2.

* cited by examiner

OIL QUALITY SENSOR AND ADAPTER FOR DEEP FRYERS

CROSS-REFERENCE TO RELATED APPLICATIONS

This application is a Continuation Application of U.S. application Ser. No. 13/923,418, filed on Jun. 21, 2013, which is a Continuation application of U.S. application Ser. No. 12/456,389, filed on Jun. 16, 2009, which issued as U.S. Pat. No. 8,497,691 on Jul. 30, 2013, and which is a Continuation-in-Part application of U.S. application Ser. No. 12/215,307, filed on Jun. 26, 2008, which claims benefit under 35 U.S.C. 119(e) of U.S. Provisional Application Ser. Nos. 60/937,513, filed on Jun. 28, 2007, and 60/995,527, filed on Sep. 27, 2007, the contents of each of which are incorporated by reference herein.

BACKGROUND OF THE DISCLOSURE

1. Field of the Disclosure

This disclosure relates to an oil quality sensor that is installed in a fryer for the purpose of indicating when the cooking oil should be changed for one or more fryer pots. This disclosure, more particularly, relates to oil quality sensor that measures an electrical property of the oil and is disposed in a filtration loop of a fryer that is external to the one or more fryer pots.

2. Description of Related Art

During use, the oil in a fryer is degraded and loses its proper cooking capacity. Specifically, the degradation is caused by oxidation, cyclic temperature increases and hydrolysis from released water. Impurities that are generated during the frying process are collectively called total polar materials (TPMs) or total polar compounds (TPCs). The TPMs are created during the deep-frying process as triglycerides break into free fatty acids and lipid molecule residues. These substances are characterized by an increased polarity and dielectric constant compared to the original triglycerides in the oil. Thus, an increased capacitance measurement of the cooking oil is indicative of an increased level of TPMs in the cooking oil.

There are several methods for testing the quality of cooking oil. Simple methods such as testing the taste, smell and color of the oil are excessively subjective, inaccurate and too time consuming. Other methods test the smoke point or viscosity of the oil. Again, while these measurements are fairly simple, they are too dependent on factors such as oil type and oil debris to be universally reliable.

Processes that include chemical or chromatographic methods are generally more comprehensive and accurate than the simpler methods. For example, currently the most widely used test tests the fatty acids that are released from glycerines during the frying process. This test depends strongly on the moisture of the frying goods. Testing for polymeric triglycerides that are formed from frying triglycerides is often time consuming and expensive.

Accordingly, there is a need for an oil quality sensor that is able to detect the level of all deterioration products or TPMs for installation in an oil return line of a fryer that uses a capacitance sensor to determine the change of dielectric constant of the cooking oil to unacceptable levels.

SUMMARY

The present disclosure provides for a sensor disposed externally to a deep fryer that is able to indirectly measure the level of TPMs in cooking oil by measuring the an electrical property of the cooking oil.

The present disclosure also provides for a capacitance sensor for a deep fryer pot that measures the capacitance of frying oil that is located in a conduit in fluid communication with the fryer pot.

The present disclosure also provides for a sensor for a deep fryer pot that is one of a capacitance sensor, a coaxial sensor or a resonant sensor that is disposed external to the fryer pot to measure an electrical property of the cooking oil when such oil flows past the sensor.

The present disclosure further provides for a sensor that measures the capacitance of the cooking oil in the return line of a fryer pot after the oil has been filtered.

The present disclosure also provides for a capacitance sensor that is disposed in the oil return line of a deep fryer that is optimally positioned to ensure that the flow of the oil cleans the sensor before measurement of the capacitance of the cooking oil.

The present disclosure further provides for a sensor that measures the capacitance of the oil and is disposed in a filtration loop between the filter pan and the return valve to be returned to a plurality of fryer pots.

The present disclosure also provides for a capacitance sensor that is in the return line of a plurality of fryer pots. The capacitance sensor repeatedly measures the capacitance of the filtered oil during the entire return flow duration and obtains an average value of the capacitance of the oil that is returned to each of the plurality of fryer pots.

The present disclosure provides for an adapter that houses a capacitance sensor for the measure of a dielectric constant. The adapter is installed between two portions of a return pipe of a fryer pot to enable filtered oil to flow past sensor for measurement before returning to the fryer pot. An indication is provided when the dielectric constant of the cooking oil has exceeded an unacceptable level.

A system for measuring the state of degradation of cooking oil or fat includes at least one fryer pot; a conduit fluidly connected to the fryer pot for transporting cooking oil from the fryer pot and returning the cooking oil back to the fryer pot. A means for re-circulating cooking oil to and from the fryer pot; and a sensor disposed in fluid communication with the conduit that measures an electrical property of the cooking oil as the cooking oil flows past the sensor and is returned to the at least one fryer pot is provided.

A system for measuring the state of degradation of cooking oil in a deep fryer includes at least one fryer pot and a conduit fluidly connected to the at least one fryer pot for carrying cooking oil from the at least one fryer pot through a filtration unit back to the at least one fryer pot. A sensor disposed in fluid communication with the conduit for measuring a dielectric constant of the cooking oil as the cooking oil is pumped between the at least one fryer pot and through the filtration unit is provided. A controller and measurement electronics in electrical communication with the sensor that computes the dielectric constant of the cooking oil for communication to a display or an alarm are provided.

A device for installation in a deep fryer for measuring the state of degradation of cooking oil includes a sensor disposed on a support surface and in fluid communication with a conduit containing cooking oil that measures an electrical property of the cooking oil. The device also includes a connector for connection to a controller and measurement electronics in electrical communication with the sensor that computes the dielectric constant of the cooking oil that flows past the sensor.

BRIEF DESCRIPTION OF THE DRAWING

Other and further benefits, advantages and features of the present disclosure will be understood by reference to the following specification in conjunction with the accompanying drawings, in which like reference characters denote like elements of structure.

DETAILED DESCRIPTION OF THE PREFERRED EMBODIMENT

Figure 1:
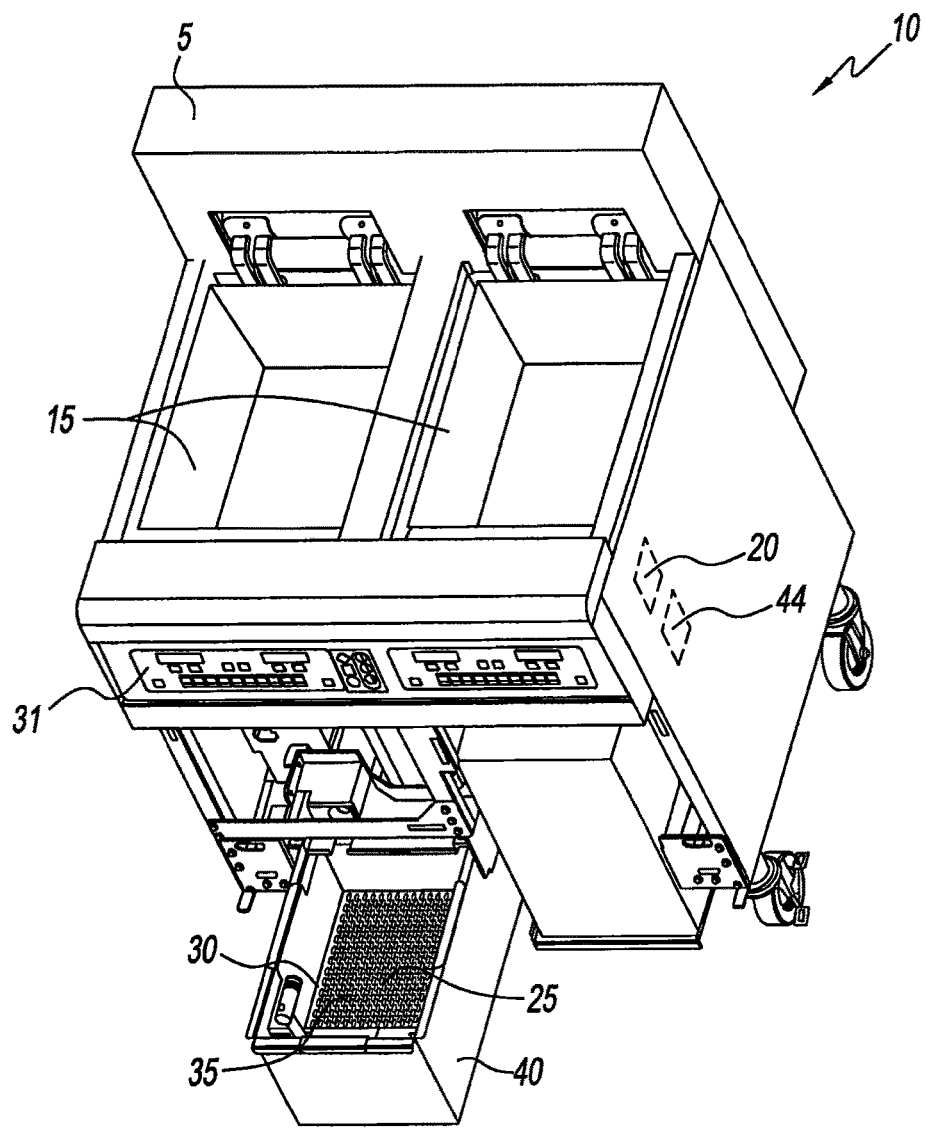
FIG. 1 illustrates an exemplary fryer housing a sensor of the present disclosure.

Referring to FIG. 1, an illustration of an exemplary fryer is shown, and generally represented by reference numeral 10. Deep fryer 10 has a housing 5, a pair of fryer pots 15 and a pair of filter pans 40. Each of the pair of filter pans 40 contains a pre-filtering medium, such as a sieve 35 that is used to remove large particles from the used cooking oil. Alternatively, both fryer pots 15 could share a common filter and return system. While fryer 10 is shown as only having two fryer pots 15, there could be as many as twelve fryer pots depending upon the needs of the food service professional. Fryer 10 also has a controller 20 for monitoring and maintaining overall operation the fryer 10. Deep fryer housing 5, also has a display panel 31 that displays various measurements of deep fryer 10 and accepts input for programming of controller 20. The present application is not limited to cooking oil, thus fat or shortening could also be used in the present application.

Figure 2:
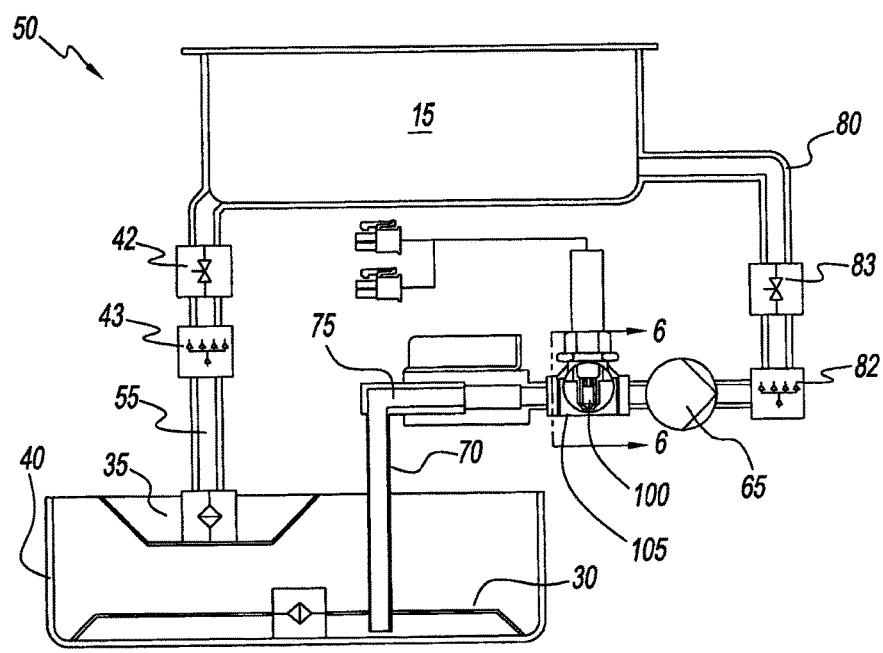
FIG. 2 illustrates an oil quality sensor according to the present disclosure incorporated into the return pipe of the filtration loop of the fryer of FIG. 1.
Figure 3:
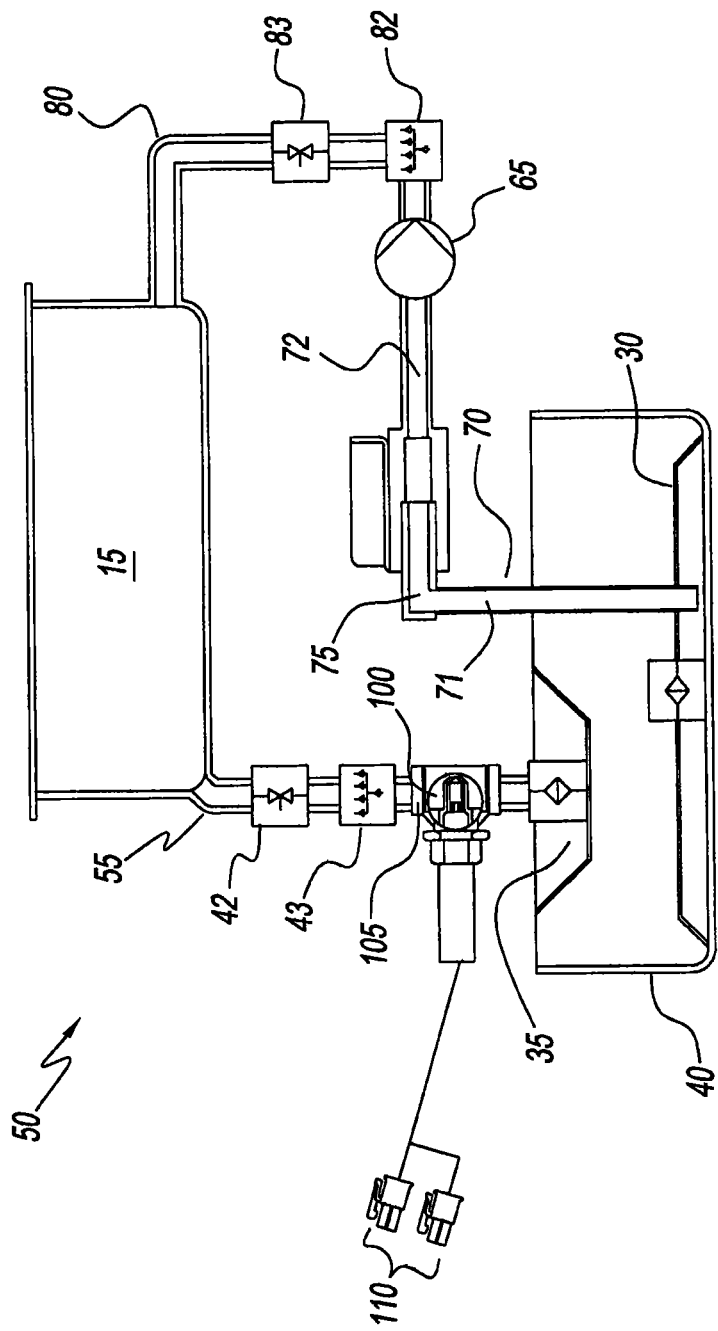
FIG. 3 illustrates an oil quality sensor according to the present disclosure incorporated into the drain pipe of the filtration loop of the fryer of FIG. 1.
Figure 4:
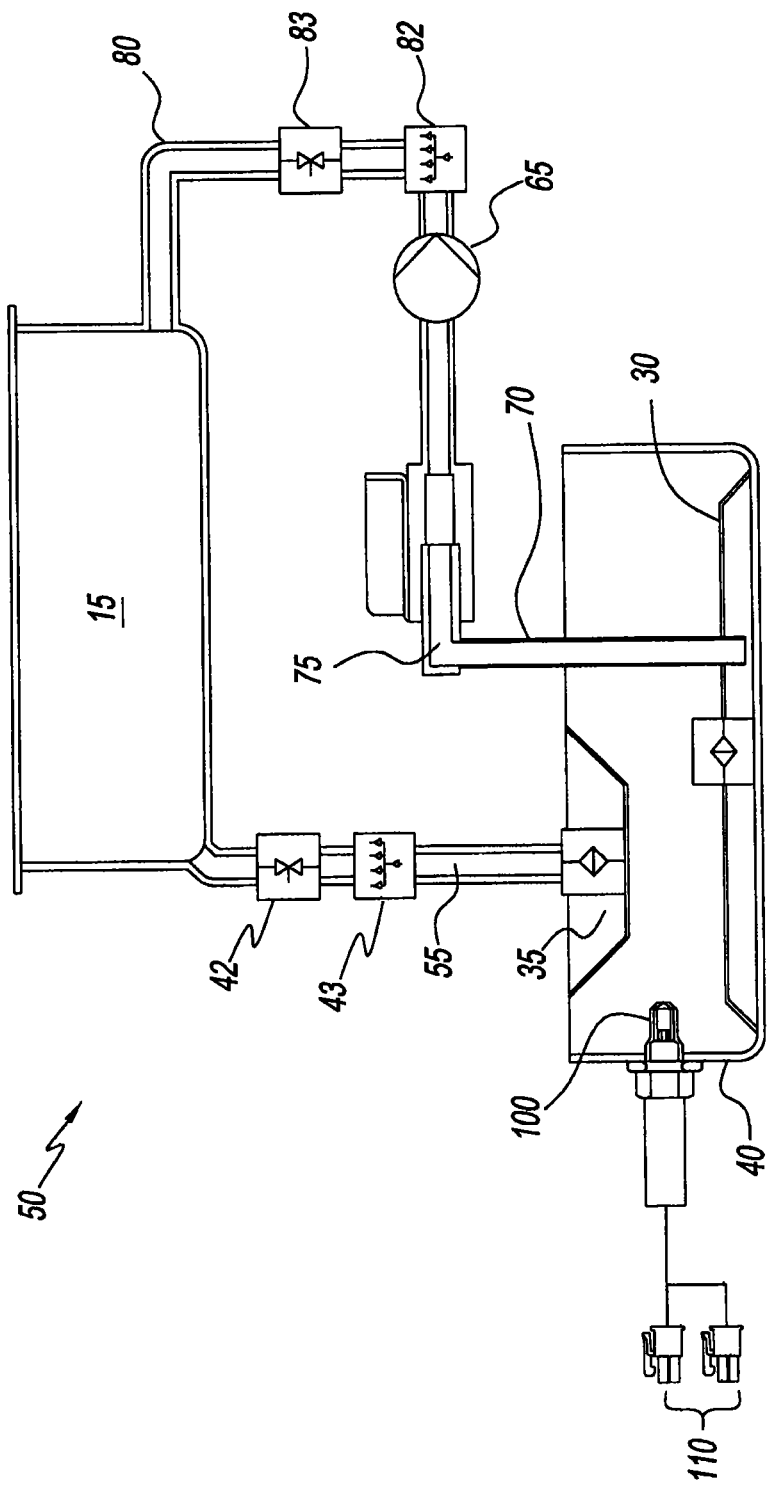
FIG. 4 illustrates an oil quality sensor according to the present disclosure incorporated into the filter pan of the filtration loop of the fryer of FIG. 1.
Figure 5:
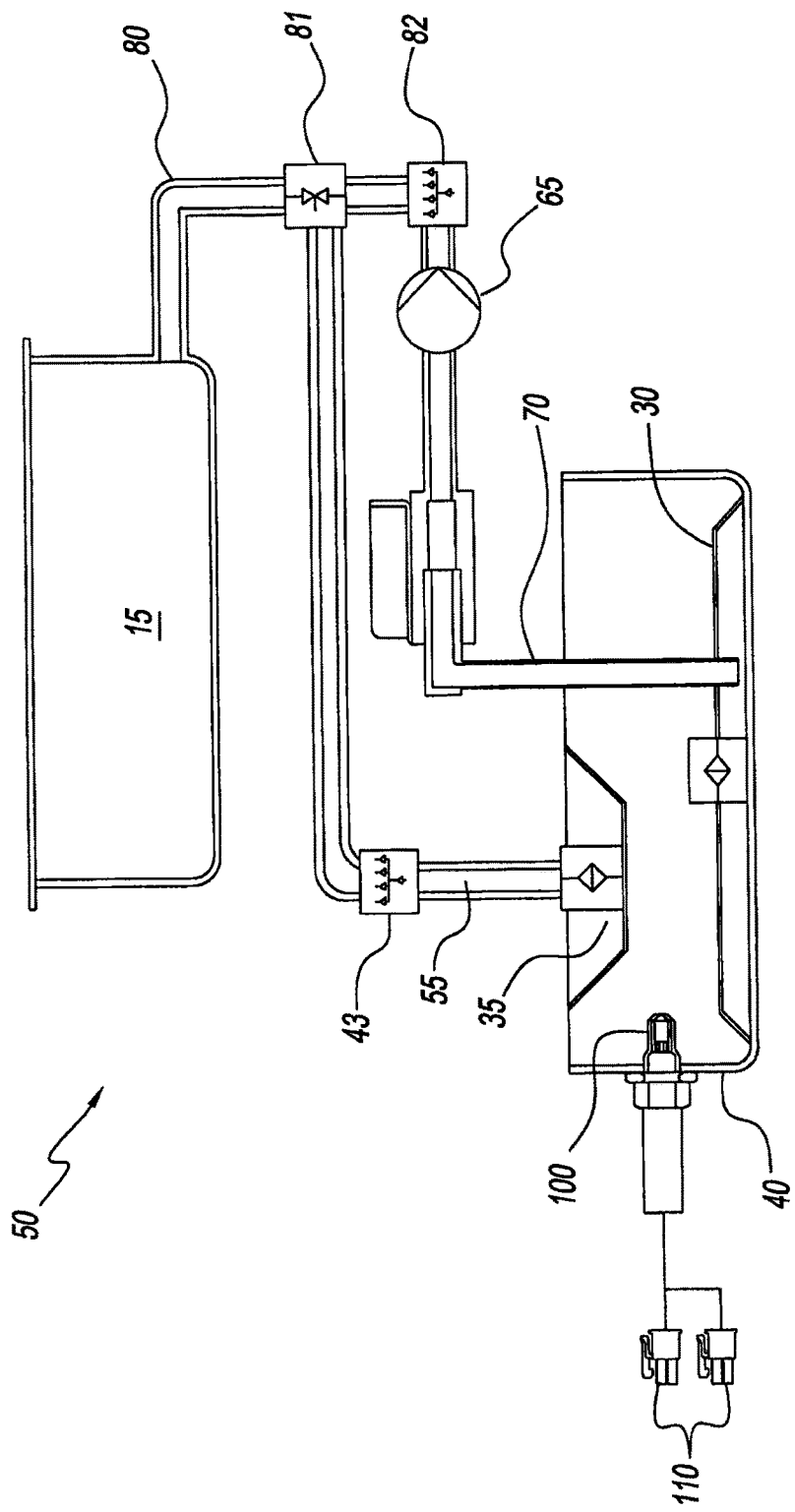
FIG. 5 illustrates an oil quality sensor according to the present disclosure incorporated into the filter pan of the filtration loop having a single pipe associated with the fryer pot.

Referring to FIG. 2, filtration loop 50 of fryer 10 incorporates a sensor and is shown, and referenced using reference numeral 100. Sensor 100 is shown in the return line 70 of filtration loop 50; however, sensor 100 preferably is disposed along filtration loop 50 external to fryer 10, in accordance with the present disclosure. Thus, sensor 100 is disposed in filtration loop 50 external to fryer pot 15 independent of the configuration of filtration loop 50, as shown in FIGS. 3 through 5. Further, sensor 100 is capable of measuring an electrical property of cooking oil 75 such as the dielectric constant, of oil. Sensor 100 is preferably one of a capacitance sensor, an open ended coaxial sensor, a conductivity or a resonant type sensor.

Referring again to FIG. 2, filtration loop 50 has a drain line 55, and a pre-filtration sieve 35, and a fine filtration pad 30. Cooking oil 75 is returned through plumbing 70 by pump 65. Prior to reaching pump 65, sensor 100 in flow of returning filtered cooking oil 75 is able to sample the an electrical property as oil 75 is being returned to fryer pot 15. A filtration loop that services multiple fryer pots would have a gate valve 42 and common drain plumbing 43 disposed upstream of pan 40 to collect used oil 75 from multiple fryer pots 15. Similarly, a return line splitter 82 and a valve 83 would direct filtered oil to specific fryer pots 15.

Referring to FIG. 3, sensor 100 is disposed in drain pipe 55 of filtration loop 50. In this embodiment, an electrical property of cooking oil 75 is repeatedly sampled as oil 75 is drained from fryer pot 15. A filtration loop 50 that services multiple fryer pots 15 would have a gate valve 42 and common drain plumbing 43 disposed upstream of pan 40 to collect used oil 75 from multiple fryer pots. Similarly, a return line splitter 82 and a valve 83 would direct filtered oil to specific fryer pots 15.

Referring to FIGS. 2, 3, 6 and 7, sensor 100 is contained within T-shaped adapter 105 that extends within housing 5 generally beneath fryer pot 15. T-shaped adapter 105 is connected in return-line of cooking oil of pipe 70. T-shaped adapter 105 is preferably connected between two portions of return pipe 70, upstream portion 71 and downstream portion 72, in a mating relationship via mating threads disposed on interconnecting portions thereof. Oil sensor 100 extends within adapter 105 and is positioned to lie in the stream of flow of oil 75, such that the flow of oil 75 from upstream portion 71, through adapter 105 to downstream portion 72 is uninterrupted. Additionally, the flow of oil 75 is coincident with longitudinal axis of upstream portion 70, downstream portion 72 and adapter 105 installed between portions 71 and 72. Oil sensor 100 extends within and is protected by adapter 105.

Referring to FIG. 4, sensor 100 is disposed in filtration loop 50, in filter pan 40. In this configuration, the dielectric constant of filtered cooking oil is sampled in pan 40 prior to passing through filtration pad 30 and returning to fryer pot 15.

Referring to FIG. 5, filtration loop 50 configuration also has sensor 100 disposed to sample an electrical property of oil external to fryer pot 15. In this configuration, sensor 100 is disposed in filtration loop 50; however, there is only a single conduit 80 that is in fluid communication with fryer pot 15. In this configuration valve 81 is a three-way valve that is controlled by controller 20 to direct cooking oil through pipe 55 during a draining cycle and to open to permit filtered oil to be pumped back and return to fryer pot via pipe 80. In this configuration, sensor 100 could have been disposed within pipe 55, or 70 external to fryer pot 15. In this configuration, pump 65 can service multiple fryer pots 15.

Oil sensor 100 is located in an adapter 105 in the filtration loop of fryer pot 15 as shown in FIGS. 2 and 3. Sensor 100 is located to measure and continuously sample an electrical property of cooking oil 75 before it re-enters fryer pot 15, independent of its location external to fryer pot 15. When the triglycerides of filtered cooking oil 75 break into fatty acids and lipid molecules during the heating and cooking cycles the polarity of oil 75 increases. The accumulation of polar materials lowers the insulating properties of cooking oil and elevates the dielectric constant of cooking oil 75 to higher values. This increased polarity correlates with an increased dielectric constant of oil 75. Thus, sensor 100 is able to measure the change of the TPM values by measuring the dielectric constant of cooking oil 75 as pump 65 returns oil to fryer pot 15. When sensor 100 detects an unacceptable level of TPMs an indication is provided to an operator to change the oil. Thus, sensor 100 ensures that oil 75 is not wasted by being prematurely changed or overused thereby tainting food and harming consumers.

Oil sensor 100 is operatively connected to measurement electronics 44 and controller 20 of fryer 10 via plugs 110. Electronics 44 and controller 20 enable periodic measurements made by sensor 100 for calculation of TPM values are averaged before oil 75 returns to fryer pot 15.

Figure 6:
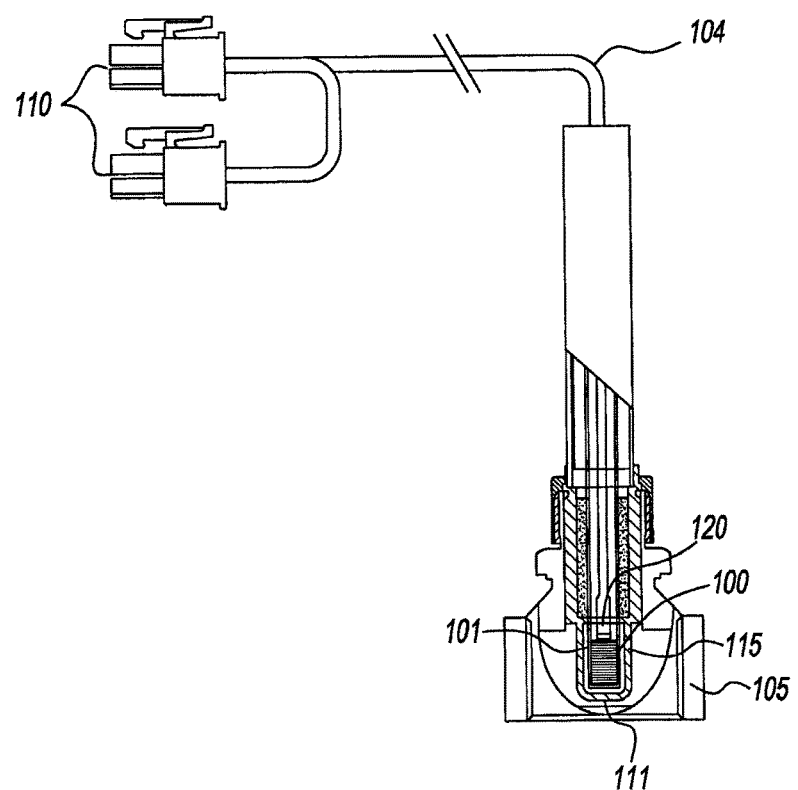
FIG. 6 illustrates a partial cross-section view of the sensor of FIG. 2 along line 6-6.
Figure 7:
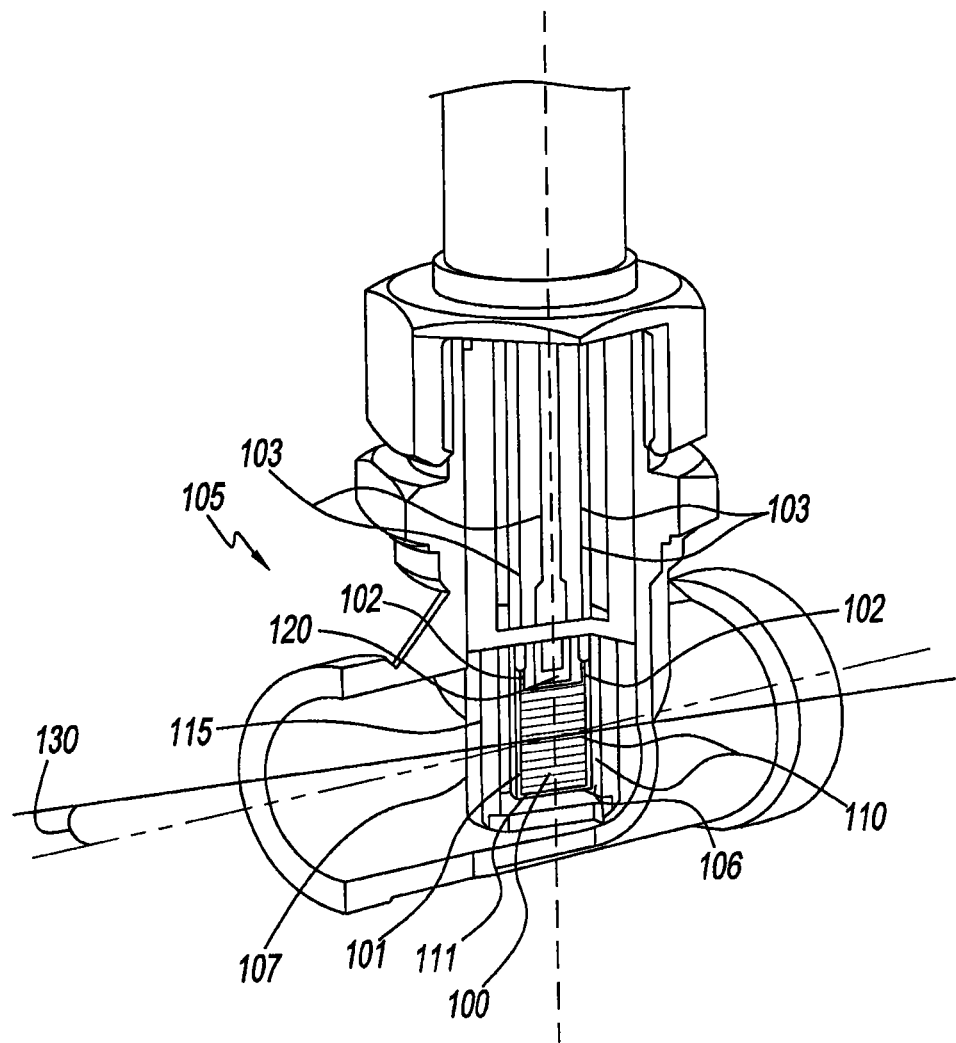
FIG. 7 illustrates a further partial cross-section view of the sensor of FIG. 2 along line 7-7.

Referring to FIGS. 6 and 7, sensor 100 is disposed on a support surface 115 that extends within adapter 105. Sensor 100, in one embodiment as a capacitor 111, is made from highly conductive wires 101 that are preferably printed onto support surface 115. Sensor 100 is configured such that a constant space is between separate highly conductive wires 101 thereby forming a capacitor 111. Highly conductive wires 101 are preferably made of gold, although other materials having highly conductive properties could also be used. Capacitor 111 is preferably printed on support surface 115 that is made from a ceramic material. Capacitor 111 has two ends 102 that are each connected to leads 103 that are also printed on support surface 115. Leads 103 are connected at one end to capacitor 101 and at the other connector end to plugs 110 via cable 104 for connection to measurement electronics 44 and controller 20. Thus, the non-conductive quality of ceramic support surface 115 provides electrical insulation between adjacent wires of capacitor 111 and leads 103. When sensor 100 is not part of an adapter 105, sensor 10 extends within filtration unit as shown in FIGS. 4 and 5.

Prior to measurements, sensor 100 achieves operational temperatures by being in the flow of quickly moving cooking oil 75 caused by pump returning oil to fryer pot 15. The quickly flowing cooking oil 75 also acts as a scrubber to clean sensor front 106 and sensor back 107 as it passes thereby to be returned to fryer pot 15. Sensor 100 must be clean to provide accurate measurements of oil capacitance and an indication of when oil must be changed. Sensor 100 must be properly positioned such that sensor front 106 and sensor back 107 are cleaned. Thus, sensor 100 and support surface 115 on which sensor 100 is disposed are, optimally positioned/angled to take advantage of the approaching flow of oil 75 that is flowing through or in-line with both portions 71 and 72 of return pipe 70. The placement angle 130 of approximately 20° to 50° relative to the direction of oil flow shown by centerline or longitudinal axis of pipe 70 having portions 71 and 72 and adapter 105 ensures that the oncoming filtered cooking oil will clean sensor front 106. Sensor 100 is cleaned by the impulse of the flow on the high pressure side in front of sensor 100 and the vortex generation of the low pressure side down-stream of sensor 100. Thus, flow of oil contacts sensor front 106 at an angle of from 20° to 50°. Were sensor 100 not properly angled, insufficient cleaning of the sensor front 106 and sensor back 107 would occur and the sensor measurements would be compromised and inaccurate. Additionally, sensor 100 must be clean to enhance the useful life of sensor 100.

Support surface 115 also includes a temperature sensor 120 proximate sensor 100. Temperature sensor 120 is preferably formed as an electrical resistor. Temperature sensor 120 is connected by electrical leads 103, as sensor 100, for connection to controller 20 and measurement electronics 44. Controller 20 continuously receives signals via amplifier and A/D converter from capacitance sensor 100 and temperature sensor 120, for measurements of oil capacitance and oil temperature. Thus, the dielectric constant of the oil is constantly being measured at various temperatures as oil flows through adapter 105 by sensor 100 at it returns to fryer pot 15. Measurements are provided to display to indicate the actual degree of decomposition of the oil 75, so that operator may know when oil should be changed.

Sensor 100 repeatedly samples TPM in cooking filtered cooking oil 75, these data are sent to measurement electronics 44 and controller 20 via cable 104 and connector 110. The measurements are averaged over the duration of the return of filtered cooking oil 75 to fryer pots 15. Thus, the calculated averaged value of the TPMs can be calculated and compared to known accurate values to detect the dielectric constant of the cooking oil. Controller 20 is capable of storing acceptable dielectric values of clean cooking oil for comparison to the measured values. Should the dielectric constant of filtered cooking oil 75 exceed a predetermined threshold, an indicator, such as an audible or visible alarm, is engaged. Additionally, display on display panel 31 shows measurements.

Optionally, visible alarms can be color-coded to indicate a level of measured dielectric acceptability. For example, a color such as green indicates good quality oil, amber would indicate that oil needs replacement shortly and red would indicate that the oil is of poor quality and needs to be immediately changed.

The present disclosure having been thus described with particular reference to the preferred forms thereof, it will be obvious that various changes and modifications may be made therein without departing from the spirit and scope of the present disclosure as defined in the appended claims.

What is claimed is:

1. A system for measuring the state of degradation of a deep fryer cooking oil in a deep fryer comprising:
    at least one fryer pot;
    at least one conduit in fluid communication with said at least one fryer pot for transporting said deep fryer cooking oil from said at least one fryer pot or returning said deep fryer cooking oil back to said at least one fryer pot;
    at least one pump for re-circulating said deep fryer cooking oil from and to said at least one fryer pot;
    an oil quality sensor that is in fluid communication with said at least one conduit to measure an electrical property of said deep fryer cooking oil when it is external to said at least one fryer pot and as said deep fryer cooking oil flows past or comes into contact with said oil quality sensor which is also positioned external to said at least one fryer pot; and
    at least one temperature sensor that is also external to said at least one fryer pot and is disposed in fluid communication with said at least one conduit and proximate to said oil quality sensor to measure a temperature of said deep fryer cooking oil as said deep fryer cooking oil flows past or comes into contact with said at least one temperature sensor.

2. The system of claim 1, wherein said oil quality sensor is a capacitance sensor, a coaxial sensor, a conductivity sensor or a resonant sensor.

3. The system of claim 1, further comprising a filtration unit, wherein said filtration unit is disposed in-line with said at least one conduit.

4. The system of claim 1, wherein said conduit comprises a single pipe that drains said deep fryer cooking oil from said at least one fryer pot and returns said deep fryer cooking oil to said at least one fryer pot via said single pipe.

5. The system of claim 1, further comprising an indicator in communication with said oil quality sensor to provide an indication of said electrical property, wherein said indicator is a display or an alarm.

6. The system of claim 1, wherein said pump is disposed either upstream or downstream of said oil quality sensor and said at least one fryer pot to pump said deep fryer cooking oil past said oil quality sensor to said at least one fryer pot.

7. The system of claim 5, wherein said alarm is an audible or visible alarm.

8. The system of claim 5, wherein a display shows measurements relating to degradation of said deep fryer cooking oil.

9. The system of claim 7, wherein said visible alarm is color-coded to indicate a level of acceptability of said electrical property of said deep fryer cooking oil.

10. The system of claim 9, wherein a color provided by said visible alarm indicates when said deep fryer cooking oil needs replacement.

11. The system of claim 5, wherein said alarm comprises a staged alarm according to different values of degradation of said deep fryer cooking oil.

12. A system for measuring the state of degradation of deep fryer cooking oil in a deep fryer comprising:
at least one fryer pot;
at least one conduit in fluid communication with said at least one fryer pot for carrying said deep fryer cooking oil from said at least one fryer pot through a filtration unit back to said at least one fryer pot;
an oil quality sensor disposed between said filtration unit and said at least one fryer pot for measuring said deep fryer cooking oil when it is external to said at least one fryer pot and after said deep fryer cooking oil has been filtered by said filtration unit, said oil quality sensor being in fluid communication with said at least one conduit for measuring an electrical property of said deep fryer cooking oil, after said deep fryer cooking oil is pumped through said filtration unit; and
a temperature sensor that is also external to said at least one fryer pot and is disposed in fluid communication with said at least one conduit to measure a temperature of said deep fryer cooking oil as the filtered deep fryer cooking oil flows past or comes into contact with said oil quality sensor.

13. The system of claim 12, wherein said oil quality sensor is disposed in an adapter that is connected to said at least one conduit.

14. The system of claim 12, further comprising a pump, wherein said pump is disposed between said oil quality sensor and said at least one fryer pot to pump said deep fryer cooking oil from said filtration unit to said at least one fryer pot.

15. A device installed in a deep fryer for measuring the state of degradation of deep fryer cooking oil in at least one fryer pot comprising:
an oil quality sensor disposed in at least one conduit with flowing said deep fryer cooking oil external to said fryer pot to measure an electrical property of said deep fryer cooking oil;
a temperature sensor that is also external to said at least one fryer pot and disposed in fluid communication with said at least one conduit to measure a temperature of said deep fryer cooking oil as said deep fryer cooking oil flows past or comes into contact with said temperature sensor; and
wherein a controller and measurement electronics are in communication with said oil quality sensor and said temperature sensor to provide measurements and to calculate and average values of said electrical property of said deep fryer cooking oil before it is returned to said at least one fryer pot.

16. The device of claim 15, wherein said oil quality sensor is one of a capacitance sensor, a coaxial sensor, a conductive sensor or a resonant sensor.

17. A system for measuring the state of degradation of a deep fryer cooking oil in a deep fryer comprising:
a plurality of fryer pots,
a filtration loop comprising a filter pan and drain plumbing that collects said deep fryer cooking oil that has been used for frying from said plurality of fryer pots and at least one return conduit that returns said deep fryer cooking oil to each of said plurality of fryer pots after said deep fryer cooking oil has been filtered;
at least one pump for re-circulating said deep fryer cooking oil through said filtration loop to and from said plurality of fryer pots;
at least one oil quality sensor external to said plurality of fryer pots and disposed in fluid communication with said deep fryer cooking oil to measure an electrical property of said deep fryer cooking oil when it is external to said fryer pots and as said deep fryer cooking oil flows past or comes into contact with said oil quality sensor and is returned to said plurality of fryer pots; and
at least one temperature sensor that is also external to said at least one fryer pot and is disposed in fluid communication with said at least one conduit and proximate to said oil quality sensor to measure a temperature of said deep fryer cooking oil when it is external to said fryer pots and as said deep fryer cooking oil flows past or comes into contact with said at least one temperature sensor,
wherein said drain plumbing comprises at least one drain pipe associated with each of said fryer pots, wherein said drain pipe transports said deep fryer cooking oil from said plurality of fryer pots, and wherein at one least return conduit returns said deep fryer cooking oil to each of said plurality of fryer pots, and
wherein said oil quality sensor and said temperature sensor are disposed in fluid communication with said filtration loop, external to said fryer pots and measures said electrical property and temperature of said deep fryer cooking oil, respectively, before said deep fryer cooking oil is returned to said plurality of fryer pots.

18. The system according to claim 17, further comprising an indicator in communication with said oil quality sensor to provide an indication when said electrical property of said deep fryer cooking oil exceeds a predetermined threshold.

* * * * *